(12) United States Patent
Nanthakumar

(10) Patent No.: US 9,636,327 B2
(45) Date of Patent: May 2, 2017

(54) METHODS OF ADMINISTERING DANTROLENE FOR THE ACUTE TREATMENT OF CARDIAC ARRHYTHMIAS

(71) Applicant: University Health Network, Toronto General Hospital, Toronto (CA)

(72) Inventor: Kumaraswamy Nanthakumar, Toronto (CA)

(73) Assignee: University Health Network, Toronto, Ontario (CA)

( * ) Notice: Subject to any disclaimer, the term of this patent is extended or adjusted under 35 U.S.C. 154(b) by 0 days.

(21) Appl. No.: 14/889,767

(22) PCT Filed: May 5, 2014

(86) PCT No.: PCT/IB2014/001748
§ 371 (c)(1),
(2) Date: Nov. 6, 2015

(87) PCT Pub. No.: WO2014/191837
PCT Pub. Date: Dec. 4, 2014

(65) Prior Publication Data
US 2016/0101085 A1  Apr. 14, 2016

Related U.S. Application Data

(60) Provisional application No. 61/820,134, filed on May 6, 2013.

(51) Int. Cl.
| | | |
|---|---|---|
| A61K 31/41 | (2006.01) | |
| A61K 31/415 | (2006.01) | |
| A61K 31/4178 | (2006.01) | |
| A61K 45/06 | (2006.01) | |
| A61K 31/422 | (2006.01) | |

(52) U.S. Cl.
CPC ........ *A61K 31/4178* (2013.01); *A61K 31/422* (2013.01); *A61K 45/06* (2013.01)

(58) Field of Classification Search
CPC ............................ A61K 8/4946; C07D 263/32

USPC ................................................. 514/364, 390
See application file for complete search history.

(56) References Cited

U.S. PATENT DOCUMENTS 4,543,359 A * 9/1985 Ellis ..................... A61K 31/415
514/390

OTHER PUBLICATIONS

International Search Report and Written Opinion, dated Dec. 23, 2014, for PCT/IB2014/001748.
Kobayashi et al.; Dantrolene, a Therapeutic Agent for Malignant Hyperthermia, Markedly Improves the Function of Failing Cardiomyocytes by Stabilizing Interdomain Interactions within the Ryanodine Receptor; Journal of the American College of Cardiology (2009), vol. 53, No. 21, p. 1993-2005.
Kobayashi et al.; Dantrolene, a Therapeutic Agent for Malignant Hyperthermia, Inhibits Catecholaminergic Polymorphic Ventricular Tachycardia in a PyR2 Knock-in Mounse Model; Circulation Journal (2010), vol. 74, p. 2579-2584.
Maxwell et al; Dantrolene prevents arrythmogenic Ca2+ release in Heart Failiuer, Am J. Physiol. Heart Circ Physiol. (2012), vol. 302, No. 4, p. H953-H963.
Zamiri, et al.; Dantrolene Improves Survival After Ventricular Fibrillation by Mitigating Impaired Calcium Handling in Animal Models; Circulation 2014, vol. 130, p. 875-885.
Roden, et al.; Dantrolene: From Better Bacon to a Treatment for Ventricular Fibrillation; Circulation 2014, vol. 130., p. 834-836.
Brooks, RR, et al., "Effects of dantrolene sodium in rodent models of cardiac arrhythmia", EP Journal of Pharmacology, Elsevier Science NO., vol. 164., No. 3, May 30, 1989, pp. 521-530.

\* cited by examiner

*Primary Examiner* — Raymond Henley, III
(74) *Attorney, Agent, or Firm* — Bryan D. Zerhusen; Locke Lord LLP

(57) ABSTRACT

The present description relates to methods of administering effective amounts of an anti-arrhythmic agent, e.g., dantrolene, azumolene or a pharmaceutically acceptable salt thereof, for the acute treatment of cardiac arrhythmias, e.g., atrial fibrillation, premature ventricular contraction, ventricular tachycardia or ventricular fibrillation, and prevention of subsequent cardiac arrhythmias, wherein the methods effectuate a reduction in morbidity and mortality.

16 Claims, 6 Drawing Sheets

(A)

(B)

METHODS OF ADMINISTERING DANTROLENE FOR THE ACUTE TREATMENT OF CARDIAC ARRHYTHMIAS

FIELD OF THE INVENTION

The present description relates to methods of administering agents for the acute treatment of cardiac arrhythmias, and for the prevention subsequent cardiac arrhythmias, e.g., ventricular tachycardia or ventricular fibrillation.

RELATED APPLICATIONS

This application claims the benefit of and priority to U.S. Provisional Patent Application No. 61/820,134 filed May 6, 2013, and International Patent Application Serial No. PCT/IB2014/001748 (i.e., PCT/US2014/036783) filed 5 May 2014, the contents of which are incorporated herein by reference.

BACKGROUND

Cardiac arrest, also known as cardiopulmonary arrest, is an abrupt cessation of pump function in the heart, and cessation of normal circulation of the blood due to failure of the heart to contract effectively. Cardiac arrest can be caused by a variety of factors including, e.g., coronary heart disease, hypertension, myocardial infarction and ischemia, atrial and ventricular arrhythmias, and heart failure.

Cardiac arrest is potentially reversible if treated early. However, if untreated, unexpected cardiac arrest can lead to death within minutes. The treatment for cardiac arrest is immediate defibrillation while cardiopulmonary resuscitation (CPR) is used to provide circulatory support. Defibrillation is performed by applying an electric shock to the heart, which resets the cells, permitting a normal beat to re-establish itself. CPR is a critical part of the management of cardiac arrest. It should be started as soon as possible and interrupted as little as possible. The component of CPR which seems to make the greatest difference is the chest compressions.

Despite significant progress in CPR methods in recent decades, survival following sudden cardiac arrest due to ventricular arrhythmias ("VA"), e.g., ventricular tachycardia ("VT") and/or ventricular fibrillation ("VF"), and subsequent advanced life support has not dramatically improved.[1] Survival from out-of-hospital cardiac arrest to hospital admission is estimated to be 23.8% with only 7.6% survival to hospital discharge.[1] Strategies for increasing survival by using adjunctive treatment and interventions such as beta-blockers or certain antiarrhythmic agents have been attempted with little success.[1-4] Shock resistant VF, refibrillation, post-shock pulseless electrical activity, and decreased myocardial contractility after resuscitation are challenges frequently observed during resuscitation from VF. Many of these factors have been shown to affect survival and morbidity.[1,4-6]

VAs are characterized by a disruption in the normal excitation-contraction rhythm of heart. In particular, VT and VF are characterized by abnormally rapid, asynchronous contraction of the ventricles. As such, the heart is unable to adequately pump oxygenated blood to the systemic circulation. If not treated immediately, VAs can lead to additional tissue damage or patient death. These potentially life threatening events are characterized by, among other things, an increase in transient calcium currents and an elevation in diastolic calcium concentration in cardiac tissue, lengthening of the cardiac action potential, a drop in blood pressure and ischemia (lack of adequate blood flow to the heart). These changes can potentially affect the return of spontaneous circulation, hemodynamics, refibrillation and resuscitation success.

Resistant ventricular fibrillation, refibrillation and diminished myocardial contractility are important factors leading to poor survival following cardiac arrest. Global ischemia from VF arrest activates multiple pathways, which leads to dysfunction of several ion channels including calcium cycling channels amongst others. For example, VA events may lead to calcium overload and myocardial dysfunction after prolonged VT or VF.

Previous studies have suggested that the cardiac-specific Ryanodine Receptor, RyR2, dysfunction diminishes cardiac contractility in a manner that is analogous to that observed in heart failure in both human and animal models.[8-10] It is proposed that a "leaky" ryanodine receptor underlies the initiation and maintenance of VT or VF.[9,11] Previous in vitro studies have suggested that prior administration of dantrolene soldium can stabilize RyR2 and confer resistance to the induction of arrhythmias. However, it is unknown whether RyR2 dysfunction can be rectified in response to, or subsequent to a VT or VF event in order to acutely treat or control arrhythmias, e.g., arrhythmias that occur subsequent to cardiac arrest. Furthermore, it is unknown whether such acute treatments can impart any protection from additional, potentially fatal arrhythmic events in order to improve hemodynamic outcomes and patient survival.

Thus, a need remains in the art for therapeutic agents and methods effective for the acute treatment of cardiac arrhythmias, e.g., ventricular arrhythmias such as VT and/or VF, such as occur following, e.g., atrial fibrillation, premature ventricular contraction, infarction, ischemia, tachycardia, heart failure or cardiac arrest. Moreover, there exists a need in the art for therapeutic interventions that prevent or abrogate additional or subsequent arrhythmias and to ameliorate their detrimental effects.

SUMMARY

The present description relates to the surprising and unexpected discovery that dantrolene, derivatives or analogs thereof, are effective for the acute treatment of cardiac arrhythmias. Moreover, the description demonstrates that dantrolene, derivatives or analogs thereof, are effective for the treatment and prevention of ventricular arrhythmias following, e.g., atrial fibrillation, premature ventricular contraction, infarction, ischemia, tachycardia, heart failure or cardiac arrest. In particular, the description demonstrates that dantrolene, derivatives or analogs thereof, can abrogate and ameliorate the detrimental effects of cardiac arrest, such as, e.g., treat or prevent ventricular arrhythmias (ventricular tachycardia or ventricular fibrillation), that typically occur subsequent to cardiac arrest. As such, the present description provides methods that surprisingly and unexpectedly improve return of spontaneous circulation, hemodynamics, and resuscitation success, reducing morbidity and mortality.

Therefore, in one aspect the description provides a method for acute treatment of a cardiac arrhythmia comprising administering a therapeutically effective amount of at least one of dantrolene, a dantrolene derivative or analog, or a pharmaceutically acceptable salt thereof to a subject in need thereof, wherein the method is effective in abrogating or ameliorating the detrimental effects of cardiac arrhythmia. In one embodiment, the methods comprise co-administering an effective amount of at least one additional antiarrhythmic agent prior, contemporaneously, or subsequent to administration of the therapeutically effective amount of dantrolene, a dantrolene derivative or analog, or a pharmaceutically acceptable salt thereof, e.g., dantrolene sodium, azumolene or combination thereof, wherein the combination is effective in treating or preventing cardiac arrhythmia and the detrimental effects that result therefrom.

In another aspect, the description provides a method for acute treatment of cardiac arrest comprising administering a therapeutically effective amount of dantrolene, a dantrolene derivative or analog, or a pharmaceutically acceptable salt thereof to a subject in need thereof, wherein the method is effective in abrogating or ameliorating the detrimental effects of cardiac arrest. In certain embodiments, the detrimental effect of cardiac arrest is a ventricular arrhythmia (VA), for example, ventricular tachycardia (VT) or ventricular fibrillation (VF). In additional embodiments, the step of administering a therapeutically effective amount of dantrolene, a dantrolene derivative or analog, or a pharmaceutically acceptable salt thereof is performed approximately contemporaneously with the onset of cardiac arrest or afterwards, for example, within about 30, 25, 20, 15, 10, 5, 1 minute(s) (and including all values in between); 60, 50, 40, 30, 20, 10, 1 second(s) (and including all values in between) of onset of cardiac arrest.

In certain embodiments of the methods described herein, the step of administering a therapeutically effective amount of dantrolene, a dantrolene derivative or analog, or a pharmaceutically acceptable salt thereof is performed approximately contemporaneously with or following a step of performing cardiopulmonary resuscitation (CPR), defibrillation or both.

In any of the aspects or embodiments described herein, the dantrolene, dantrolene derivative or analog, or a pharmaceutically acceptable salt thereof is dantrolene sodium, azumolene or a combination of both.

In any of the aspects or embodiments described herein, the therapeutically effective amount of dantrolene, a dantrolene derivative or analog, or a pharmaceutically acceptable salt thereof is in the range of from 0.1 µg/kg/day to about 1000 mg/kg/day.

In any of the aspects or embodiments described herein, the subject in need thereof is, e.g., a mammal such as a human, that is experiencing or has recently experienced cardiac arrest.

In an additional aspect, the description provides a method for acute treatment of cardiac arrest comprising administering a therapeutically effective amount of at least one of dantrolene sodium, azumolene or a combination thereof to a subject approximately during or following cardiac arrest, wherein the method is effective in treating or preventing ventricular arrhythmia and the detrimental effects that result therefrom. In certain embodiments, the ventricular arrhythmia is a VT or VF. In additional embodiments, the step of administering a therapeutically effective amount of dantrolene, azumolene or combination thereof, is performed contemporaneously with or following a step of performing cardiopulmonary resuscitation (CPR), defibrillation or both.

In any of the aspects or embodiments described herein, the methods further comprise co-administration of a therapeutically effective amount of at least one additional anti-arrhythmic agent administered prior, contemporaneously, or subsequent to administration of the therapeutically effective amount of the dantrolene, dantrolene derivative or analog, or a pharmaceutically acceptable salt thereof.

In any of the aspects or embodiments described herein, the methods further effectuate at least one of an improvement in the time-dependent temporal disorganization of VF, enhanced defibrillation success, an improvement in hemodynamic performance, improved sinus rhythm after defibrillation, improvement in sustained return of spontaneous circulation (ROSC), reduction of time to ROSC, improved post-defibrillation systolic blood pressure, improved post-defibrillation diastolic blood pressure, reduced time to successful defibrillation, reduced energy needed for defibrillation, reduced number of defibrillations required, reduced duration of fibrillation, improved survival rate, improved cardiac contractility, reduction in refibrillations, reduction in calcium amplitude alternans (CaA-ALT), reduction in RyR2 hyperphosphorylation, reduction in RyR2 calcium leak, increased resistance to VF induction, improved survival or a combination thereof.

In an additional aspect, the description provides a method for acute treatment of cardiac arrest comprising: performing CPR or defibrillation or both on a subject in need thereof; and administering a therapeutically effective amount of at least one of dantrolene sodium, azumolene or a combination thereof to the subject approximately contemporaneously with or subsequent to performing step (i), wherein the method is effective for abrogating or ameliorating a detrimental effects of cardiac arrest. In certain embodiments, the detrimental effect of cardiac arrest is ventricular arrhythmia, e.g., VT or VF. In additional embodiments, the method further effectuates at least one of a reduction in RyR2 hyperphosphorylation, a reduction in calcium alternans, a reduction in refibrillations, an improvement in cardiac contractility, an improvement in ROSC, an improvement in hemodynamic function, a reduction in morbidity, a reduction in mortality, or a combination thereof.

In another aspect the description provides a method for the treatment of premature ventricular contraction (PVC) induced left ventricular (LV) dysfunction comprising administering a therapeutically effective amount of at least one of dantrolene sodium, azumolene or a combination thereof to a subject approximately during or following a PVC event, wherein the method is effective in treating or preventing PVC induced left ventricular (LV) dysfunction. In certain embodiments, the effective amount of dantrolene sodium or azumolene is from 0.1 µg/kg/day to about 1000 mg/kg/day. In an additional embodiment, the methods comprise co-administering an effective amount of at least one additional anti-arrhythmic agent prior, contemporaneously, or subsequent to administration of the therapeutically effective amount of dantrolene sodium, azumolene or combination thereof, wherein the combination is effective in treating or preventing PVC induced left ventricular (LV) dysfunction and the detrimental effects that result therefrom.

In yet another aspect the description provides a method for the treatment of atrial fibrillation (AF) induced left ventricular (LV) dysfunction comprising administering a therapeutically effective amount of at least one of dantrolene sodium, azumolene or a combination thereof to a subject approximately during or following AF, wherein the method is effective in treating or preventing AF induced left ventricular (LV) dysfunction and the detrimental effects that result therefrom. In certain embodiments, the effective amount of dantrolene sodium or azumolene is from 0.1 µg/kg/day to about 1000 mg/kg/day. In an additional embodiment, the methods comprise co-administering an effective amount of at least one additional anti-arrhythmic agent prior, contemporaneously, or subsequent to administration of the therapeutically effective amount of dantrolene sodium, azumolene or combination thereof, wherein the combination is effective in treating or preventing AF induced left ventricular (LV) dysfunction and the detrimental effects that result therefrom.

A composition comprising a pharmaceutically acceptable carrier and an effective amount of at least one of dantrolene, azumolene, a dantrolene derivative, analog, pharmaceutically acceptable salt thereof or combination thereof for use in treating a condition in a subject selected from cardiac arrest, cardiac arrhythmia, premature ventricular contraction (PVC) induced left ventricular dysfunction, atrial fibrillation induced left ventricular dysfunction and a combination thereof.

A composition comprising a pharmaceutically acceptable carrier and an effective amount of at least one of dantrolene, azumolene, a dantrolene derivative, analog, pharmaceutically acceptable salt thereof or combination thereof for use in a treatment or therapy to treat or ameliorate a condition in a subject selected from cardiac arrest, cardiac arrhythmia, premature ventricular contraction (PVC) induced left ventricular dysfunction, atrial fibrillation induced left ventricular dysfunction and a combination thereof, wherein the treatment or therapy includes administering the composition approximately during or following cardiac arrest, cardiac arrhythmia, premature ventricular contraction (PVC) induced left ventricular dysfunction, atrial fibrillation induced left ventricular dysfunction, wherein the method is effective in treating or preventing left ventricular (LV) dysfunction and the detrimental effects that result therefrom.

Use of a composition comprising a pharmaceutically acceptable carrier and an effective amount of at least one of dantrolene, azumolene, a dantrolene derivative, analog, pharmaceutically acceptable salt thereof or combination thereof for the manufacture of a medicament for a treatment or therapy to treat or ameliorate a condition in a subject selected from cardiac arrest, cardiac arrhythmia, premature ventricular contraction (PVC) induced left ventricular dysfunction, atrial fibrillation induced left ventricular dysfunction and a combination thereof, wherein the treatment or therapy includes administering the composition approximately during or following cardiac arrest, cardiac arrhythmia, premature ventricular contraction (PVC) induced left ventricular dysfunction, atrial fibrillation induced left ventricular dysfunction, wherein the method is effective in treating or preventing left ventricular (LV) dysfunction and the detrimental effects that result therefrom.

In any of the embodiments described herein, the effective amount of dantrolene, azumolene, a dantrolene derivative, analog, pharmaceutically acceptable salt thereof or combination thereof can be from 0.1 µg/kg/day to about 1000 mg/kg/day.

The present description further provides any invention described herein.

The preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention. The publications and other materials used herein to illuminate the background of the invention, and in particular cases, to provide additional details respecting the practice, are incorporated by reference, and for convenience are listed in the appended bibliography.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

Figure 1:
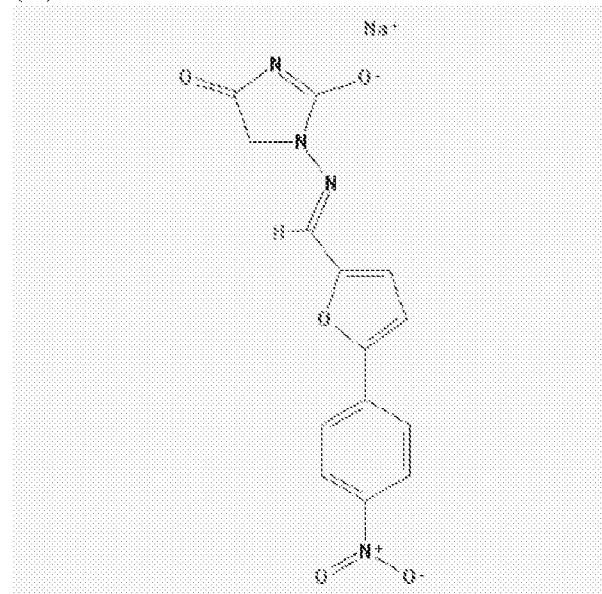
FIG. 1. Structure of dantrolene and exemplary dantrolene analog. (A) Dantrolene sodium [Molecular Formula: $C_{14}H_9N_4NaO_5$]; 1-[[[5-(4-nitrophenyl)-2-furanyl]methylene]amino]-2,4-imidazolidinedione sodium salt; (B) Azumolene, a more water-soluble analog of dantrolene. Azumolene has a bromine residue instead of the nitro group found in dantrolene, and is 30 times more water-soluble FIG. 2. Changes in systolic (Left) and diastolic (Right) blood pressure throughout the experiment in dantrolene and Control group. The data presented only includes survivors (normal sinus rhythm at 30 min after termination of VF). VF0: BP during first min of VF, VF4: BP during the $4^{th}$ min of VF, CPR0: BP during first min of CPR, CPR3: BP during the $3^{rd}$ min of CPR, *: P>0.05 vs. control, ++: P<0.0003 vs. control, P<0.04 vs. post-defibrillation, †: P<0.04 vs. control, **: P<0.005 vs. control, ++: P<0.02 vs. control, #: P<0.0003 vs. control, P<0.0008 vs. post-defibrillation FIG. 3. Changes in heart rate post-defibrillation in survivors. The heart rate was lower in dantrolene group but except for heart rate at 20 min post-defibrillation, the difference was not statistically significant between groups. *: P<0.05 vs. control.
Figure 1:
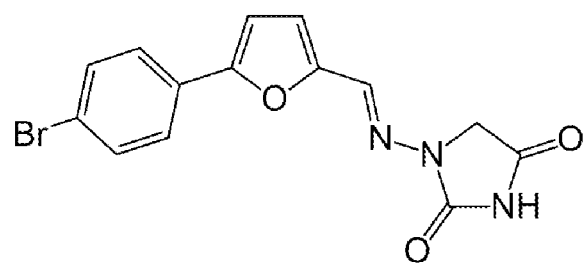

versus 0.87 in Controls (n=6). (P=NS) (1), Phosphorylated-RyR2/GAPDH ratio was significantly lower in dantrolene-treated hearts. (0.4 vs. 1.02) (2), **: P<0.008 vs. Controls.

DETAILED DESCRIPTION

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. Ranges from any lower limit to any upper limit are contemplated. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

All numerical values within the detailed description and the claims herein are modified by "about" or "approximately" the indicated value, and take into account experimental error and variations that would be expected by a person having ordinary skill in the art.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

I. EXEMPLARY DEFINITIONS

Unless defined otherwise, all technical and scientific terms used herein have the meaning commonly understood by a person skilled in the art to which this invention belongs. The appended references, the entire disclosures of which are incorporated herein by reference, provide one of skill with a general definition of many of the terms used in this invention.

As used herein, the following terms may have meanings ascribed to them below, unless specified otherwise. However, it should be understood that other meanings that are known or understood by those having ordinary skill in the art are also possible, and within the scope of the present invention. All publications, patent applications, patents, and other references mentioned herein are incorporated by reference in their entirety. In the case of conflict, the present specification, including definitions, will control. In addition, the materials, methods, and examples are illustrative only and not intended to be limiting.

"Derivatives" is used throughout the specification to describe compounds formed from the native compounds either directly, by modification, or by partial substitution. For example, in certain embodiments, a derivative is a pharmaceutically acceptable prodrug form (such as an ester, amide other prodrug group) which, upon administration to a patient, provides directly or indirectly the present compound or an active metabolite of the present compound. "Analogs" are compounds that have a structure similar to, but not identical to, the native compound.

The terms "treat", "treating", and "treatment", etc., as used herein, refer to any action providing a benefit to a patient for which the present compounds may be administered, including the amelioration of the detrimental effects of cardiac arrest in the patient or subject.

The term "coadministration" or "combination therapy" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. In certain preferred aspects of the present invention, one or more of the compounds described herein, are coadministered in combination with at least one additional bioactive agent having anti-arrhythmic activity. In particularly preferred aspects of the invention, the co-administration of compounds results in synergistic anti-arrhythmic activity and/or therapy.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present invention.

The term "effective" is used to describe an amount of a compound, composition or component which, when used within the context of its intended use, effects an intended result.

The term "patient" or "subject" is used throughout the specification to describe an animal, preferably a human or a domesticated animal, to whom treatment, including prophylactic treatment, with the compositions according to the present invention is provided. For treatment of those infections, conditions or disease states which are specific for a specific animal such as a human patient, the term patient refers to that specific animal. In general, in the present invention, the term patient refers to a human patient unless otherwise stated or implied from the context of the use of the term.

The term "compound", as used herein, unless otherwise indicated, refers to any specific chemical compound disclosed herein and includes tautomers, regioisomers, geometric isomers, and where applicable, stereoisomers, including optical isomers (enantiomers) and other steroisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity.

II. METHODS

Each heart beat originates as an electrical impulse from a small area of tissue in the right atrium of the heart called the sinus node or Sino-atrial node or SA node. The impulse initially causes both atria to contract, then activates the atrioventricular (or AV) node which is normally the only electrical connection between the atria and the ventricles (main pumping chambers). The impulse then spreads through both ventricles via the Bundle of His and the Purkinje fibers causing a synchronized contraction of the heart muscle and, thus, the pulse.

Cardiac dysrhythmia (also known as arrhythmia or irregular heartbeat) is any of a large and heterogeneous group of conditions in which there is abnormal electrical activity in the heart. The heartbeat may be too fast or too slow, and may be regular or irregular. A heart beat that is too fast is called tachycardia and a heartbeat that is too slow is called bradycardia.

Although many arrhythmias are not life-threatening, some can cause cardiac arrest. For example, injured heart tissue conducts electrical impulses more slowly than normal heart tissue. The difference in conduction velocity between injured and uninjured tissue can trigger re-entry or a feedback loop that is believed to be the cause of many lethal arrhythmias. The most serious of these arrhythmias is ventricular fibrillation (V-FibNF), an extremely fast and chaotic heart rhythm that is the leading cause of sudden cardiac death. Another life-threatening arrhythmia is ventricular tachycardia (V-Tach/VT), which may or may not cause sudden cardiac death. However, ventricular tachycardia usually results in rapid heart rates that prevent the heart from pumping blood effectively. Cardiac output and blood pressure may fall to dangerous levels, which can lead to further coronary ischemia and extension of the infarct.

The current standard of care for ventricular arrhythmias (e.g., VT or VF), includes CPR and defibrillation. The cardiac defibrillator is a device that was specifically designed to terminate these potentially fatal arrhythmias.

The device works by delivering an electrical shock to the patient in order to depolarize a critical mass of the heart muscle, in effect "rebooting" the heart. This therapy is time dependent, and the odds of successful defibrillation decline rapidly after the onset of cardiopulmonary arrest.

As indicated above, cardiac arrest, also known as cardiopulmonary arrest or circulatory arrest, is an abrupt cessation of pump function in the heart, and cessation of normal circulation of the blood due to failure of the heart to contract effectively. Cardiac arrest can be caused by a variety of factors including, e.g., coronary heart disease, hypertension, myocardial infarction and ischemia, arrhythmias, and heart failure.

Myocardial infarction (MI) or acute myocardial infarction (AMI), commonly known as a heart attack, results from the partial interruption of blood supply to a part of the heart muscle, causing the heart cells to be damaged or die. This is most commonly due to occlusion (blockage) of a coronary artery following the rupture of a vulnerable atherosclerotic plaque, which is an unstable collection of cholesterol and fatty acids and white blood cells in the wall of an artery. The resulting ischemia (restriction in blood supply) and ensuing oxygen shortage, if left untreated for a sufficient period of time, can cause damage or death (infarction) of heart muscle tissue (myocardium). Typical symptoms of acute myocardial infarction include sudden retrosternal chest pain (typically radiating to the left arm or left side of the neck), shortness of breath, nausea, vomiting, palpitations, sweating, and anxiety (often described as a sense of impending doom). Women may experience fewer typical symptoms than men, most commonly shortness of breath, weakness, a feeling of indigestion, and fatigue. A sizeable proportion of myocardial infarctions (approximately 22-64%) are "silent", that is without chest pain or other symptoms. Among the diagnostic tests available to detect heart muscle damage are an electrocardiogram (ECG), echocardiography, cardiac MRI and various blood tests. The most often used blood markers are the creatine kinase-MB (CK-MB) fraction and the troponin levels.

If impaired blood flow to the heart lasts long enough, it triggers a process called the ischemic cascade; the heart cells in the territory of the occluded coronary artery die (chiefly through necrosis) and do not grow back. A collagen scar forms in its place. Recent studies indicate that another form of cell death called apoptosis also plays a role in the process of tissue damage subsequent to myocardial infarction. As a result, the patient's heart will be permanently damaged. This myocardial scarring also puts the patient at risk for potentially life threatening arrhythmias, and may result in the formation of a ventricular aneurysm that can rupture with catastrophic consequences.

Arrhythmias can occur in the upper chambers of the heart, (atria), or in the lower chambers of the heart, (ventricles). Arrhythmias may occur at any age. Some are barely perceptible, whereas others can be more dramatic and can even lead to cardiac arrest and sudden cardiac death. Significantly, cardiac arrhythmias are one of the most common causes of death when travelling to a hospital. Thus, the methods described herein can reduce morbidity and mortality associated with dangerous arrhythmias and cardiac arrest.

In adults and children over 15, resting heart rate faster than 100 beats/minute is labelled tachycardia. Tachycardia may result in palpitation; however, tachycardia is not necessarily an arrhythmia. Increased heart rate is a normal response to physical exercise or emotional stress. This is mediated by the sympathetic nervous system on the sinus node and called sinus tachycardia. Other things that increase sympathetic nervous system activity in the heart include ingested or injected substances, such as caffeine or amphetamines, and an overactive thyroid gland (hyperthyroidism).

Tachycardia that is not sinus tachycardia usually results from the addition of abnormal impulses to the normal cardiac cycle. Abnormal impulses can begin by one of three mechanisms: automaticity, reentry or triggered activity. A specialized form of re-entry problem is termed fibrillation.

Automaticity refers to a cardiac muscle cell firing off an impulse on its own. All of the cells in the heart have the ability to initiate an action potential; however, only some of these cells are designed to routinely trigger heart beats. These cells are found in the conduction system of the heart and include the SA node, AV node, Bundle of His and Purkinje fibers. The sinoatrial node is a single specialized location in the atrium which has a higher automaticity (a faster pacemaker) than the rest of the heart and, therefore, is usually responsible for setting the heart rate and initiating each heartbeat.

Any part of the heart that initiates an impulse without waiting for the sinoatrial node is called an ectopic focus and is, by definition, a pathological phenomenon. This may cause a single premature beat now and then, or, if the ectopic focus fires more often than the sinoatrial node, it can produce a sustained abnormal rhythm. Rhythms produced by an ectopic focus in the atria, or by the atrioventricular node, are the least dangerous dysrhythmias; but they can still produce a decrease in the heart's pumping efficiency, because the signal reaches the various parts of the heart muscle with different timing than usual and can be responsible for poorly coordinated contraction.

Re-entrant arrhythmias occur when an electrical impulse recurrently travels in a tight circle within the heart, rather than moving from one end of the heart to the other and then stopping. Every cardiac cell is able to transmit impulses of excitation in every direction but will only do so once within a short time. Normally, the action potential impulse will spread through the heart quickly enough that each cell will only respond once. However, if there is some essential heterogeneity of refractory period or if conduction is abnormally slow in some areas (for example in heart damage) so the myocardial cells are unable to activate the fast sodium channel, part of the impulse will arrive late and potentially be treated as a new impulse. Depending on the timing, this can produce a sustained abnormal circuit rhythm. As a sort of re-entry, the vortices of excitation in the myocardium (autowave vortices) is considered to be the main mechanism of life-threatening cardiac arrhythmias. In particular, the autowave reverberator is a typical in thin walls of the atria, with the atrial flutter producing. Re-entry are also responsible for most paroxysmal supraventricular tachycardia, and dangerous ventricular tachycardia. These types of re-entry circuits are different from WPW syndromes in which the real pathways existed.

When an entire chamber of the heart is involved in a multiple micro-reentry circuits and, therefore, quivering with chaotic electrical impulses, it is said to be in fibrillation. Fibrillation can affect the atrium (atrial fibrillation) or the ventricle (ventricular fibrillation); ventricular fibrillation is imminently life-threatening. Atrial fibrillation affects the upper chambers of the heart, known as the atria. Atrial fibrillation may be due to serious underlying medical conditions and should be evaluated by a physician. It is not typically a medical emergency. Ventricular fibrillation occurs in the ventricles (lower chambers) of the heart; it is always a medical emergency. If left untreated, ventricular fibrillation (VF, or V-fib) can lead to death within minutes. When a heart goes into V-fib, effective pumping of the blood stops. V-fib is considered a form of cardiac arrest. An individual suffering from it will not survive unless cardiopulmonary resuscitation (CPR) and defibrillation are provided immediately. CPR can prolong the survival of the brain in the lack of a normal pulse, but defibrillation is the only intervention that can restore a healthy heart rhythm.

As described herein, it was surprising and unexpectedly found that dantrolene improved the time-dependent temporal disorganization of VF and enhanced defibrillation success in subjects suffering from cardiac arrhythmia or cardiac arrest. For example, subjects treated with dantrolene required fewer shocks and had better hemodynamic outcomes and higher survival rate. Dantrolene also led to fewer and in addition, did not alter refractoriness. Most importantly, in rabbit hearts, dantrolene decreased CaA-ALT and mitigated hyperphosphorylation of RYR2 during VF. Furthermore, dantrolene-treated rabbit hearts were more resistant to VF induction. Taken together these findings suggest a potential novel strategy of using dantrolene for improving resuscitation outcomes. These findings are surprising, especially, in view of previous studies that indicate dantrolene is arrhythmogenic.[29]

The present description relates to the surprising and unexpected discovery that dantrolene, derivatives or analogs thereof (See FIGS. 1A and B), are effective for the acute treatment of cardiac arrhythmia, e.g., ventricular arrhythmia such as VT or VF. Moreover, the description demonstrates that dantrolene, derivatives or analogs thereof, are effective for the treatment and prevention of cardiac arrhythmias following, e.g., atrial fibrillation, premature ventricular contraction, infarction, ischemia, tachycardia, heart failure or cardiac arrest. In particular, the description demonstrates that dantrolene, derivatives or analogs thereof, can abrogate and ameliorate the detrimental effects of cardiac arrhythmias, including ventricular arrhythmias (ventricular tachycardia or ventricular fibrillation), that typically occur subsequent to, e.g., atrial fibrillation, premature ventricular contraction, infarction, ischemia, tachycardia, heart failure or cardiac arrest. As such, the present description provides methods that surprisingly and unexpectedly improve return of spontaneous circulation, hemodynamics, and resuscitation success, reducing morbidity and mortality.

Dantrolene sodium (1-[[5-(p-nitrophenyl)furfurylidene]-amino]hydantoin sodium salt) (FIG. 1A) is described in U.S. Pat. No. 3,415,821, incorporated herein by reference in its entirety. Historically, dantrolene sodium has been used as a skeletal muscle relaxant particularly in controlling the manifestations of clinical spasticity resulting from upper neuron disorders. (Physicians' Desk Reference, 36th Edition, 1982). Formulations comprising therapeutically effective amounts of dantrolene sodium are known to those of skill in the art as described in U.S. Patent Publication 2009/0093531, which is incorporated herein by reference.

Dantrolene has been safely used in clinical practice with little side effects for many years. In the current study we showed that Dantrolene decreases RYR2 hyperphosphorylation, calcium alternans, number of refibrillations and improves cardiac contractility, ROSC following defibrillation. Thus it could serve as a novel strategy to improve survival following VF arrest.

Thus, in one aspect the description provides a method for acute treatment of a cardiac arrhythmia comprising administering a therapeutically effective amount of at least one of dantrolene, a dantrolene derivative or analog, or a pharmaceutically acceptable salt thereof to a subject in need thereof, wherein the method is effective in abrogating or ameliorating the detrimental effects of cardiac arrhythmia. In one embodiment, the methods comprise co-administering an effective amount of at least one additional anti-arrhythmic agent prior, contemporaneously, or subsequent to administration of the therapeutically effective amount of dantrolene, a dantrolene derivative or analog, or a pharmaceutically acceptable salt thereof, e.g., dantrolene sodium, azumolene or combination thereof, wherein the combination is effective in treating or preventing cardiac arrhythmia and the detrimental effects that result therefrom.

In any of the embodiments described herein, the subject is a mammal. In still another embodiment, the subject is a human.

In another aspect, the description provides a method for acute treatment of cardiac arrest comprising administering a therapeutically effective amount of dantrolene, a dantrolene derivative or analog, or a pharmaceutically acceptable salt thereof to a subject in need thereof, wherein the method is effective in abrogating or ameliorating the detrimental effects of cardiac arrest. In certain embodiments, the detrimental effect of cardiac arrest is a ventricular arrhythmia (VA), for example, ventricular tachycardia (VT) or ventricular fibrillation (VF). In additional embodiments, the step of administering a therapeutically effective amount of dantrolene, a dantrolene derivative or analog, or a pharmaceutically acceptable salt thereof is performed approximately contemporaneously with the onset of cardiac arrest or afterwards, for example, within about 30, 25, 20, 15, 10, 5, 1 minute(s) (and including all values in between); 60, 50, 40, 30, 20, 10, 1 second(s) (and including all values in between) of onset of cardiac arrest. In still an additional embodiment, the step of administering a therapeutically effective amount of dantrolene, a dantrolene derivative or analog, or a pharmaceutically acceptable salt thereof is performed approximately contemporaneously with the onset of cardiac arrest or afterwards, for example, within about 60, 50, 40, 30, 20, 10, 1 seconds (and including all values in between) of onset of cardiac arrest.

In any of the aspects or embodiments of the methods described herein, the step of administering a therapeutically effective amount of dantrolene, a dantrolene derivative or analog, or a pharmaceutically acceptable salt thereof is performed approximately contemporaneously with or following a step of performing cardiopulmonary resuscitation (CPR), defibrillation or both.

In any of the aspects or embodiments described herein, the therapeutically effective amount of dantrolene, a dantrolene derivative or analog, or a pharmaceutically acceptable salt thereof is administered in one or more doses. Furthermore, in any of the aspects or embodiments described herein, the therapeutically effective amount of dantrolene, a dantrolene derivative or analog, or a pharmaceutically acceptable salt thereof is administered in a suitable pharmaceutically acceptable form. In a preferred embodiment, the therapeutically effective amount of dantrolene, a dantrolene derivative or analog, or a pharmaceutically acceptable salt thereof is administered as an injectable liquid.

In any of the aspects or embodiments described herein, the dantrolene, dantrolene derivative or analog, or a pharmaceutically acceptable salt thereof is dantrolene sodium, azumolene or a combination of both.

In any of the aspects or embodiments described herein, the therapeutically effective amount of dantrolene, a dantrolene derivative or analog, or a pharmaceutically acceptable salt thereof is in the range of from 0.1 µg/kg/day to about 1000 mg/kg/day.

In any of the aspects or embodiments described herein, the subject in need thereof is, e.g., a mammal such as a human, that is experiencing or has recently experienced cardiac arrest.

In an additional aspect, the description provides a method for acute treatment of cardiac arrest comprising administering a therapeutically effective amount of at least one of dantrolene sodium, azumolene or a combination thereof to a subject approximately during or following cardiac arrest, wherein the method is effective in treating or preventing ventricular arrhythmia. In certain embodiments, the ventricular arrhythmia is a VT or VF. In additional embodiments, the step of administering a therapeutically effective amount of dantrolene sodium, azumolene or combination thereof, is performed contemporaneously with or following a step of performing cardiopulmonary resuscitation (CPR), defibrillation or both.

A composition comprising a pharmaceutically acceptable carrier and an effective amount of at least one of dantrolene, azumolene, a dantrolene derivative, analog, pharmaceutically acceptable salt thereof or combination thereof for use in treating a condition in a subject selected from cardiac arrest, cardiac arrhythmia, premature ventricular contraction (PVC) induced left ventricular dysfunction, atrial fibrillation induced left ventricular dysfunction and a combination thereof.

A composition comprising a pharmaceutically acceptable carrier and an effective amount of at least one of dantrolene, azumolene, a dantrolene derivative, analog, pharmaceutically acceptable salt thereof or combination thereof for use in a treatment or therapy to treat or ameliorate a condition in a subject selected from cardiac arrest, cardiac arrhythmia, premature ventricular contraction (PVC) induced left ventricular dysfunction, atrial fibrillation induced left ventricular dysfunction and a combination thereof, wherein the treatment or therapy includes administering the composition approximately during or following cardiac arrest, cardiac arrhythmia, premature ventricular contraction (PVC) induced left ventricular dysfunction, atrial fibrillation induced left ventricular dysfunction, wherein the method is effective in treating or preventing left ventricular (LV) dysfunction and the detrimental effects that result therefrom.

Use of a composition comprising a pharmaceutically acceptable carrier and an effective amount of at least one of dantrolene, azumolene, a dantrolene derivative, analog, pharmaceutically acceptable salt thereof or combination thereof for the manufacture of a medicament for a treatment or therapy to treat or ameliorate a condition in a subject selected from cardiac arrest, cardiac arrhythmia, premature ventricular contraction (PVC) induced left ventricular dysfunction, atrial fibrillation induced left ventricular dysfunction and a combination thereof, wherein the treatment or therapy includes administering the composition approximately during or following cardiac arrest, cardiac arrhythmia, premature ventricular contraction (PVC) induced left ventricular dysfunction, atrial fibrillation induced left ventricular dysfunction, wherein the method is effective in treating or preventing left ventricular (LV) dysfunction and the detrimental effects that result therefrom.

In any of the embodiments described herein, the effective amount of dantrolene, azumolene, a dantrolene derivative, analog, pharmaceutically acceptable salt thereof or combination thereof can be from 0.1 µg/kg/day to about 1000 mg/kg/day.

Moreover, in any of the embodiments of uses or methods described herein, performance of the use or method can further effectuate at least one of an improvement in the time-dependent temporal disorganization of VF, enhanced defibrillation success, an improvement in hemodynamic performance, improved sinus rhythm after defibrillation, improvement in sustained return of spontaneous circulation (ROSC), reduction of time to ROSC, improved post-defibrillation systolic blood pressure, improved post-defibrillation diastolic blood pressure, reduced time to successful defibrillation, reduced energy needed for defibrillation, reduced number of defibrillations required, reduced duration of fibrillation, improved survival rate, improved cardiac contractility, reduction in refibrillations, reduction in calcium amplitude alternans (CaA-ALT), reduction in RyR2 hyperphosphorylation, reduction in RyR2 calcium leak, increased resistance to VF induction, improved survival or a combination thereof.

An effective amount, pharmaceutically effective dose, therapeutically effective amount, or pharmaceutically effective amount is that dose required to prevent, inhibit the occurrence, or treat (alleviate a symptom to some extent, preferably all of the symptoms) of a disease state or pathological condition. The effective amount depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 1000 mg/kg body weight/day of active ingredients is administered dependent upon potency of the negatively charged polymer. In addition, effective amounts of the compositions of the invention encompass those amounts utilized in the examples to facilitate the intended or desired biological effect.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The formulations can be administered orally, topically, parenterally, by inhalation or spray, e.g., via dantrolene aerosol, or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present. Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

In any of the aspects or embodiments described herein, the methods further comprise co-administration of a therapeutically effective amount of at least one additional antiarrhythmic agent administered prior, contemporaneously, or subsequent to administration of the therapeutically effective amount of the dantrolene, dantrolene derivative or analog, or a pharmaceutically acceptable salt thereof. Exemplary antiarrhythmic agents that are suitable for use with the methods described herein are provided below.

There are many classes of antiarrhythmic medications, with different mechanisms of action and many different individual drugs within these classes. Although the goal of drug therapy is to prevent arrhythmia, nearly every antiarrhythmic drug has the potential to act as a pro-arrhythmic, and so must be carefully selected and used under medical supervision. A number of other drugs can be useful in cardiac arrhythmias. Several groups of drugs slow conduction through the heart, without actually preventing an arrhythmia. These drugs can be used to "rate control" a fast rhythm and make it physically tolerable for the patient.

The class I antiarrhythmic agents interfere with the sodium channel. Class I agents are grouped by what effect they have on the Na$^+$ channel, and what effect they have on cardiac action potentials. Class I agents are called Membrane Stabilizing agents. The 'stabilizing' word is used to describe the decrease of excitogenicity of the plasma membrane which is brought about by these agents. Class I agents are divided into three groups (Ia, Ib and Ic) based upon their effect on the length of the action potential: Ia lengthens the action potential (right shift); Ib shortens the action potential (left shift); Ic does not significantly affect the action potential (no shift)

Class II agents are conventional beta blockers. They act by blocking the effects of catecholamines at the $\beta_1$-adrenergic receptors, thereby decreasing sympathetic activity on the heart. These agents are particularly useful in the treatment of supraventricular tachycardias. They decrease conduction through the AV node.

Class III agents predominantly block the potassium channels, thereby prolonging repolarization. Since these agents do not affect the sodium channel, conduction velocity is not decreased. The prolongation of the action potential duration and refractory period, combined with the maintenance of normal conduction velocity, prevent re-entrant arrhythmias. (The re-entrant rhythm is less likely to interact with tissue that has become refractory). Drugs include: bretylium, amiodarone, ibutilide, sotalol, dofetilide, and dronedarone Inhibiting potassium channels, slowing repolarization, results in slowed atrial-ventricular myocyte repolarization. Class III agents have the potential to prolong the QT interval of the EKG.

Class IV agents are slow calcium channel blockers. They decrease conduction through the AV node, and shorten phase two (the plateau) of the cardiac action potential. They thus reduce the contractility of the heart, so may be inappropriate in heart failure. However, in contrast to beta blockers, they allow the body to retain adrenergic control of heart rate and contractility.

Class V agents do not generally fit into the other categories. However, they are more frequently identified by their precise mechanism.

TABLE 1

Five main classes of antiarrhythmic agents.

| Class | Known as | Examples | Mechanism | Clinical uses in cardiology |
|---|---|---|---|---|
| Ia | fast-channel blockers-affect QRS complex | Quinidine Procainamide Disopyramide | (Na$^+$) channel block (intermediate association/dissociation) | Ventricular arrhythmias prevention of paroxysmal recurrent atrial fibrillation (triggered by vagal overactivity) procainamide in Wolff-Parkinson-White syndrome |
| Ib | Do not affect QRS complex | Lidocaine Phenytoin Mexiletine Tocainide | (Na$^+$) channel block (fast association/dissociation) | treatment and prevention during and immediately after myocardial infarction, though this practice is now discouraged given the increased risk of asystole ventricular tachycardia atrial fibrillation |
| Ic | | Flecainide Propafenone Moricizine | (Na$^+$) channel block (slow association/dissociation) | prevents paroxysmal atrial fibrillation treats recurrent tachyarrhythmias |

TABLE 1-continued

Five main classes of antiarrhythmic agents.

| Class | Known as | Examples | Mechanism | Clinical uses in cardiology |
|---|---|---|---|---|
| | | | | of abnormal conduction system. contraindicated immediately post-myocardial infarction. |
| II | Beta-blockers | Propranolol Esmolol Timolol Metoprolol Atenolol Bisoprolol | beta blocking Propranolol also shows some class I action | decrease myocardial infarction mortality prevent recurrence of tachyarrhythmias |
| III | | Amiodarone Sotalol Ibutilide Dofetilide Dronedarone E-4031 | $K^+$ channel blocker Sotalol is also a beta blocker[3] Amiodarone has Class I, II, III & IV activity | In Wolff-Parkinson-White syndrome (sotalol:) ventricular tachycardias and atrial fibrillation (Ibutilide:) atrial flutter and atrial fibrillation |
| IV | slow-channel blockers | Verapamil Diltiazem | $Ca^{2+}$ channel blocker | prevent recurrence of paroxysmal supraventricular tachycardia reduce ventricular rate in patients with atrial fibrillation |
| V | | Adenosine Digoxin Magnesium Sulfate | Work by other or unknown mechanisms (Direct nodal inhibition). | Used in supraventricular arrhythmias, especially in Heart Failure with Atrial Fibrillation, contraindicated in ventricular arrhythmias. Or in the case of Magnesium Sulfate, used in Torsades de Pointes. |

In any of the aspects or embodiments described herein, the methods further effectuate at least one of an improvement in the time-dependent temporal disorganization of VF, enhanced defibrillation success, an improvement in hemodynamic performance, improved sinus rhythm after defibrillation, improvement in sustained return of spontaneous circulation (ROSC), reduction of time to ROSC, improved post-defibrillation systolic blood pressure, improved post-defibrillation diastolic blood pressure, reduced time to successful defibrillation, reduced energy needed for defibrillation, reduced number of defibrillations required, reduced duration of fibrillation, improved survival rate, improved cardiac contractility, reduction in refibrillations, reduction in calcium amplitude alternans (CaA-ALT), reduction in RyR2 hyperphosphorylation, reduction in RyR2 calcium leak, increased resistance to VF induction, improved survival or a combination thereof.

In an additional aspect, the description provides a method for acute treatment of cardiac arrest comprising: performing CPR or defibrillation or both on a subject in need thereof; and administering a therapeutically effective amount of at least one of dantrolene sodium, azumolene or a combination thereof to the subject approximately contemporaneously with or subsequent to performing step (i), wherein the method is effective for abrogating or ameliorating a detrimental effects of cardiac arrest. In certain embodiments, the detrimental effect of cardiac arrest is ventricular arrhythmia, e.g., VT or VF. In additional embodiments, the method further effectuates at least one of a reduction in RyR2 hyperphosphorylation, a reduction in calcium alternans, a reduction in refibrillations, an improvement in cardiac contractility, an improvement in ROSC, an improvement in hemodynamic function, a reduction in morbidity, a reduction in mortality, or a combination thereof.

In an additional aspect, the description provides a method for the acute treatment of premature ventricular contraction (PVC). PVC, also known as a premature ventricular complex, ventricular premature contraction (or complex or complexes) (VPC), ventricular premature beat (VPB), or ventricular extrasystole (VES), is a relatively common event where the heartbeat is initiated by Purkinje fibres in the ventricles rather than by the sinoatrial node, the normal heartbeat initiator. The electrical events of the heart detected by the electrocardiogram allow a PVC to be easily distinguished from a normal heart beat.

A PVC may be perceived as a "skipped beat," a strong beat, or felt as palpitations in the chest. They may also cause chest pain, a faint feeling, fatigue, or hyperventilation after exercise. Several PVCs in a row becomes a form of ventricular tachycardia (VT), which is a dangerous rapid heartbeat.

In a normal heartbeat, the ventricles contract after the atria have helped to fill them by contracting; in this way the ventricles can pump a maximized amount of blood both to the lungs and to the rest of the body. In a PVC, the ventricles contract first and before the atria have optimally filled the ventricles with blood, which means that circulation is inefficient. However, single beat PVC arrhythmias do not usually pose a danger and can be asymptomatic in healthy individuals.

Some possible causes of PVCs include, inter alia, myocardial infarction and Ischemia; certain medicines such as digoxin, which increases heart contraction, Myocarditis; Cardiomyopathy, hypertrophic or dilated; Myocardial contusion; Hypoxia; Hypercapnia ($CO_2$ poisoning); Sarcoidosis; Smoking; Alcohol; Drugs such as cocaine; Caffeine; Theobromine; Tricyclic antidepressants; Magnesium and potassium deficiency; Calcium excess; Thyroid problems; Chemical (electrolyte) problems in the blood; Heart attack; Adrenaline excess; Lack of sleep/exhaustion; Stress When looking at an electrocardiograph premature ventricular contractions are easily spotted and therefore a definitive diagnosis can be made. The QRS and T waves look very different to normal readings. The spacing between the PVC and the preceding QRS wave is a lot shorter than usual and the time between the PVC and the proceeding QRS is a lot longer. However, the time between the preceding and proceeding QRS waves stays the same as normal due to the compensatory pause. PVCs can be distinguished from premature atrial contractions because the compensatory pause is longer following premature ventricular contractions.

There are four different named patterns of regularly occurring PVCs. Depending whether there are 1, 2, or 3 normal beats between each PVC, the rhythm is called bigeminy, trigeminy, or quadrigeminy. A unifocal PVC is where the depolarisation is triggered from the one site in the ventricle causing the peaks on the ECG to look the same. Multifocal PVCs arise when more than one site in the ventricles initiate depolarisation causing each peak on the ECG to have a different shape. If 3 or more PVCs occur in a row it may be called Ventricular tachycardia.

There are a number of different molecular explanations for PVCs. One explanation is most basically due to an increased amount of cyclic AMP (cAMP) in the ventricular cardiac myocytes leading to increased flow of calcium ions into the cell.

Thus, in another aspect the description provides a method for the treatment of premature ventricular contraction (PVC) induced ventricular dysfunction, e.g., left ventricular (LV) dysfunction, comprising administering a therapeutically effective amount of at least one of dantrolene sodium, azumolene or a combination thereof to a subject approximately during or following a PVC event, wherein the method is effective in treating or preventing PVC induced LV dysfunction. In certain embodiments, the effective amount of dantrolene sodium or azumolene is from 0.1 µg/kg/day to about 1000 mg/kg/day. In an additional embodiment, the methods comprise co-administering an effective amount of at least one additional anti-arrhythmic agent prior, contemporaneously, or subsequent to administration of the therapeutically effective amount of dantrolene sodium, azumolene or combination thereof, wherein the combination is effective in treating or preventing PVC induced LV dysfunction.

Atrial fibrillation (AF or A-fib) is the most common cardiac arrhythmia (irregular heart beat). It may cause no symptoms, but it is often associated with palpitations, fainting, chest pain, or congestive heart failure. However, in some people atrial fibrillation is caused by otherwise idiopathic or benign conditions. Although the electrical impulses of AF occur at a high rate, most of them do not result in a heartbeat. A heart beat results when an electrical impulse from the atria passes through the atrioventricular (AV) node to the ventricles and causes them to contract. During AF, if all of the impulses from the atria passed through the AV node, there would be severe ventricular tachycardia resulting in severe reduction of cardiac output. This dangerous situation is prevented by the AV node since its limited conduction velocity reduces the rate at which impulses reach the ventricles during AF In general, AF is treated with medications to either slow the heart rate to a normal range ("rate control") or revert the heart rhythm back to normal ("rhythm control"). Synchronized electrical cardioversion can be used to convert AF to a normal heart rhythm. Surgical and catheter-based therapies may be used to prevent recurrence of AF in certain individuals. Depending on the risk of stroke and systemic embolism, people with AF may use anticoagulants such as warfarin, which substantially reduces the risk but may increase the risk of major bleeding, mainly in geriatric patients. The prevalence of AF in a population increases with age, with 8% of people over 80 having AF. Chronic AF leads to a small increase in the risk of death.

In yet another aspect the description provides a method for the treatment of atrial fibrillation (AF) induced LV dysfunction comprising administering a therapeutically effective amount of at least one of dantrolene sodium, azumolene or a combination thereof to a subject approximately during or following AF, wherein the method is effective in treating or preventing AF induced LV dysfunction. In certain embodiments, the effective amount of dantrolene sodium or azumolene is from 0.1 µg/kg/day to about 1000 mg/kg/day. In an additional embodiment, the methods comprise co-administering an effective amount of at least one additional anti-arrhythmic agent prior, contemporaneously, or subsequent to administration of the therapeutically effective amount of dantrolene sodium, azumolene or combination thereof, wherein the combination is effective in treating or preventing AF induced LV dysfunction.

The present description further provides any invention described herein.

III. EXAMPLES

It should be appreciated that the exemplary embodiments of the present invention should not be construed to be limited to the examples that are now described; rather, the exemplary embodiments of the present invention should be construed to include any and all applications provided herein and all variations within the skill of the ordinary artisan.

Dantrolene Increased Survival Following VF.

VF was successfully induced in all animals. Two of the cases developed non-sustained VT and AV dissociation before VF was induced and were eliminated from the study. Sinus rhythm immediately post-defibrillation was achieved in approximately 90.91% in Dantrolene group compared to approximately 54.55% in Controls. (P=0.05) Sustained ROSC was achieved in approximately 90.91% in Dantrolene group versus approximately 27.27% in Controls. (P<0.002) (Table 2).

Dantrolene Improved Hemodynamic Outcomes Following CPR.

Figure 2:
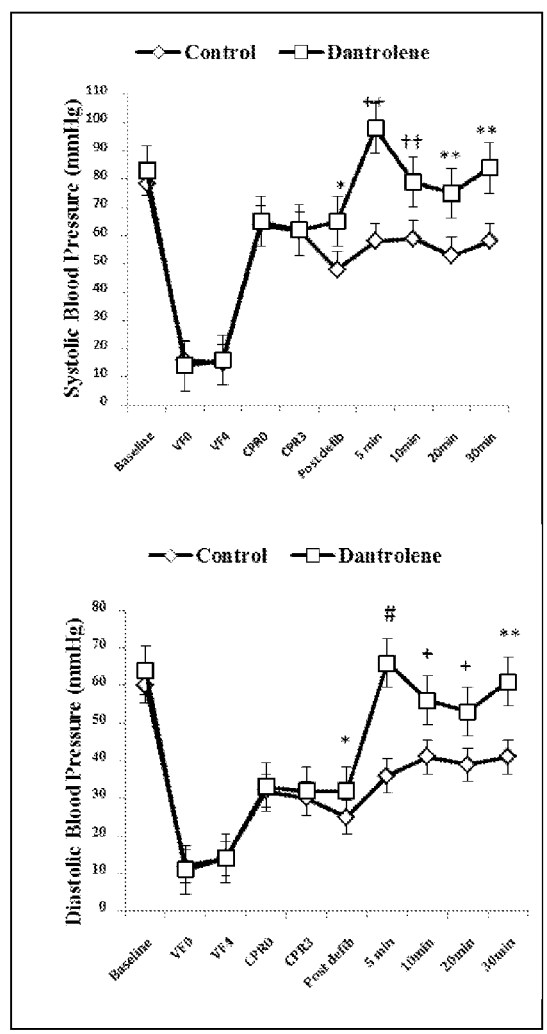
Figure 3:
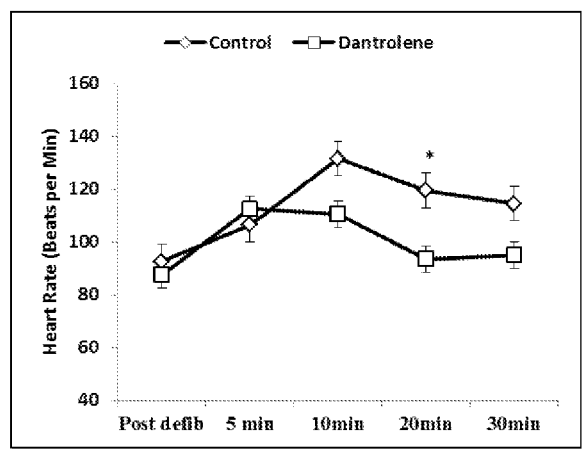

Time to ROSC was significantly shorter in Dantrolene group. (about 224 sec vs. about 426 sec, P<0.005) Additionally, Time to ROSC calculated from immediately post-defibrillation was also significantly shorter. (about 13±4 sec vs. about 103±44 sec, P<0.02) Both sBP and dBP were significantly higher during the post-defibrillation period in Dantrolene group compared to controls. Both sBP and dBP continued to rise in Dantrolene group and remained significantly higher than controls throughout the experiment. (FIG. 2) The mean sBP and dBP at the end of experiment was about 84±11 and about 61±10 mmHg in survivors in Dantrolene group and about 64±10 and about 45±6 mmHg in Controls respectively. (P<0.003 and P<0.008).

Dantrolene Enhanced Defibrillation Success.

Mean time to successful defibrillation in Dantrolene group was significantly less than controls. (about 224 sec vs. about 317 sec, P<0.03) Lower energy levels were needed in Dantrolene group for defibrillating the initial VF. Ninety percent in Dantrolene group required energy levels approximately ≤200J compared to about 45.45% of controls. (P<0.02)(Table 2).

TABLE 2

Summary of hemodynamic parameters in Dantrolene and Control groups

|  | Control | Dantrolene | P value |
|---|---|---|---|
| Successful defibrillation | 90% | 100% | NS |
| Final Rhythm |  |  | NS |
| Sinus | 54.54% | 90.91% |  |
| PEA | 18.18% | 0% |  |
| VF (or VrF) | 27.27% | 9.09% |  |
| Time to defibrillation* (sec) | 317 ± 38 | 224 ± 18 | <0.03 |
| ROSC (at 5 min post-defibrillation) | 18.18% | 90.91% | <0.001 |
| Sustained ROSC | 27.27% | 90.91% | <0.003 |
| Time to ROSC† | 426 ± 73 | 224 ± 13 | <0.005 |
| Total time in VF‡ |  |  |  |
| Excluding VrF | 598 ± 40 | 466 ± 18 | <0.009 |
| Including VrF | 654 ± 39 | 478 ± 19 | <0.0009 |
| Number of shocks (>2 attempts) | 54.55% | 9.09% | <0.02 |
| Maximum energy level | 256 ± 89J | 187 ± 62J | <0.04 |
| Total energy level | 728 ± 200 | 366 ± 139 | NS |

*Time to successful defibrillation was calculated from the onset of CPR,
†Time to ROSC was calculated from the onset of CPR until sBP of >60 mmHg was achieved after successful defibrillation,
‡Total time in VF includes the duration of initial VF plus all refibrillations observed during the experiment.
PEA: Pulseless Electrical Activity,
ROSC: Return of Spontaneous Circulation,
VrF: Ventricular Refibrillation Dantrolene Decreased Refibrillations And Improved Outcomes Following Refibrillation.

The number of refibrillation episodes was significantly lower in Dantrolene group. (Table 3) Additionally, refibrillations were easier to defibrillate in Dantrolene group with all refibrillations terminated with first defibrillation attempt. Duration of refibrillations was significantly lower in Dantrolene group. (32±6 sec vs. 112±20 sec, P<0.01)

TABLE 3

Comparison of Refibrillation parameters between Dantrolene and Control groups.

|  | Control | Dantrolene | P value |
|---|---|---|---|
| Refibrillation Incidence | 70% | 36.36% | NS |
| Number of Refibrillations | 2 ± 0.6 | 0.6 ± 0.4 | 0.05 |
| Time to onset of Refibrillation (sec) | 638 ± 252 | 51 ± 9 | <0.03 |
| Survival after Refibrillation | 57.4% (4) | 100% (3) | NS |
| Number of shocks to terminate refibrillations | 1.66 ± 0.5 | 1 ± 0 | <0.04 |
| Refibrillation duration (sec) | 112 ± 20 | 32 ± 6 | <0.01 |
| Total time in VF (sec) Including refibrillation | 654 ± 39 | 478 ± 19 | <0.0009 |

Dantrolene Organized VF Signals And Facilitated Defibrillation.

Figure 4:
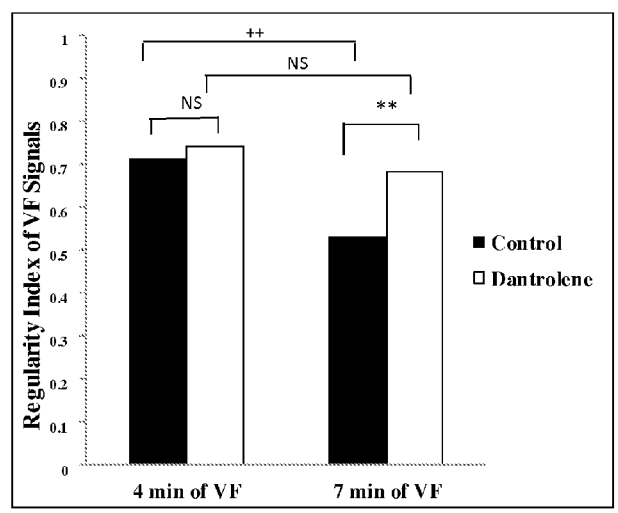
FIG. 4. Comparison of changes in VF organization during CPR between groups. Regularity Index (RI) was measured at 4 min of VF (prior to CPR) and 7 min of VF (3 min after drug infusion, prior to defibrillation). Lower RI values correlates with higher disorganization of VF signals. RI at 7 min of VF was 0.68 and 0.53 in dantrolene and Control group respectively. (**: P<0.002) VF signal organization reduced significantly during CPR in Controls (++: P<0.005) but not in dantrolene group (P>0.05).

VF signals were significantly more organized VF in Dantrolene group at about 7 min of VF. (FIG. 4) (RI approximately 0.68±0.029 vs. approximately 0.53±0.03, P<0.002). Higher organization of VF signals was responsible for earlier defibrillation success in Dantrolene-treated pigs. (approximately 89% of the effect of Dantrolene on earlier defibrillation was correlated with its effect on RI at about 7 min of VF.) (Sobel Coefficient: −78, STE: 39.1, P<0.045).

Dantrolene Did Not Alter Refractoriness.

There was no significant difference in post-defibrillation VERP between Dantrolene and Controls. (about 215±9 msec vs. about 206±4 msec, P>0.05) No significant difference in terms of QT interval or Repolarization dispersion was detected between groups. In Dantrolene group, QT interval at baseline and post-defibrillation was about 432±48 msec and about 334±83 msec while in Controls, the corresponding values were about 442±50 msec and about 325±6 msec Respectively. (P>0.05) Tp-Tn values as a measure of repolarization dispersion was measured at baseline and after defibrillation. In Dantrolene group Tp-Tn was about 68±23 msec at baseline and about 84±22 msec post-defibrillation compared to about 73±14 msec and about 85±17 msec in controls respectively. (P>0.05)

Ex-Vivo Rabbit Protocol

Dantrolene-Treated Hearts were Resistant to VF.

Figure 5:
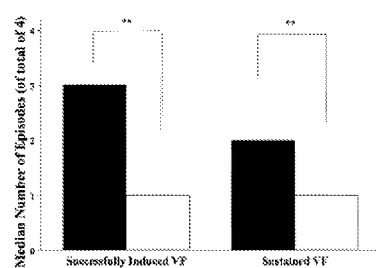
FIG. 5. Lower incidence of successfully induced or sustained VF and increased alternans threshold in dantrolene-treated rabbit hearts. (1) Out of 4 VF episodes attempted on each rabbit heart (after drug or saline infusion), the median number of successfully induced VF (≥10 sec) and sustained-VF (≥60 sec) episodes was significantly lower in dantrolene-treated hearts. (**: P<0.01), (2) Top: An ECG sample of a successfully induced VF in a control heart, Middle: Self-termination of VF after 20 seconds in a dantrolene-treated heart, Bottom: After dantrolene infusion burst pacing resulted in short duration of VF transforming into monomorphic-VT. (3) Recording of Calcium signals was acquired after 30 sec of continuous pacing at 300 bpm after $1^{st}$ and $2^{nd}$ VF episodes. Middle: CaA-ALT (in LV) emerged after $1^{st}$ VF. Bottom: Upon dantrolene infusion, alternans was abolished.
Figure 5:
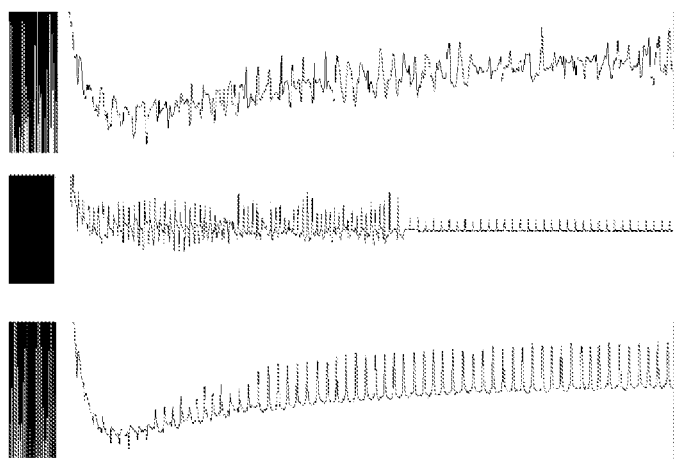
Figure 5:
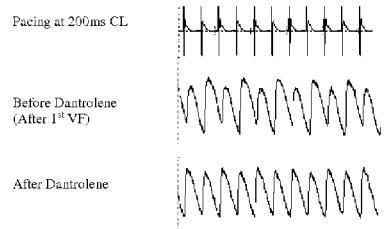

Dantrolene-treated hearts were more resistant to induction of subsequent VF episodes. In total, 21 (84%) of 25 attempts to induce VF in controls were successful (VF lasting approximately ≥10 sec) compared to 38.7% (12 of 31 attempts) in Dantrolene-treated hearts. (P<0.004, repeated measures logistic regression). Most VF episodes self-terminated and broke into sinus rhythm or monomorphic VT after infusion of Dantrolene. (FIG. 5) Moreover, VF was harder to sustain in Dantrolene group and the mean duration of all VF episodes combined was significantly shorter in Dantrolene-treated hearts. (about 194±234 sec vs. about 542±276 sec, P<0.02) Of total 25 attempts to induce VF in control hearts, 18 (72%) episodes sustained >60 sec compared to 22.58% (7 of 31 attempts) in Dantrolene-treated hearts. (P<0.006)

Dantrolene Decreased Incidence of Calcium Alternans.

After first VF episode, Calcium Amplitude Alternans (CaA-ALT) occurred in about 71.4% and about 33.33% of Controls and Dantrolene-treated hearts respectively (P>0.05). Incidence of CaA-ALT after second VF was significantly lower in Dantrolene-treated hearts (approximately 12.5% vs. approximately 80%, P<0.015). Additionally, alternans threshold significantly increased and alternans emerged at faster heart rates in Dantrolene-treated hearts (about 186±11 msec CL vs. about 255±51 msec CL, P<0.03).

Dantrolene Decreased CaMKII-Dependent Phosphorylation of RyR2.

Figure 6:
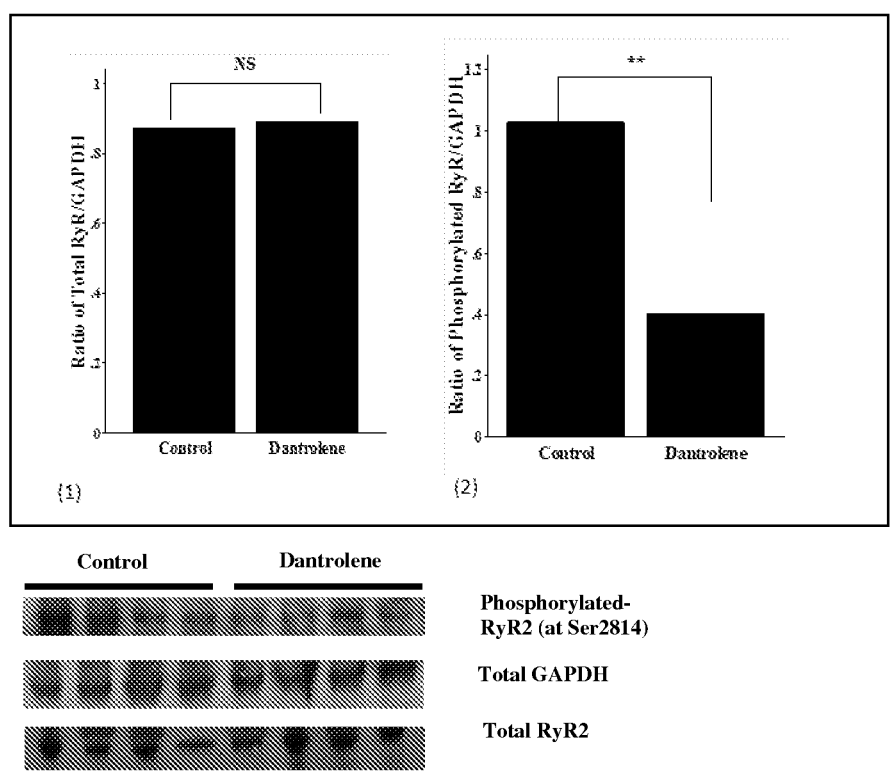
FIG. 6. Phosphorylation of RyR2 at Ser2814 between dantrolene treated and control rabbit hearts. Ratio of Total RyR2 to GAPDH was 0.88 in dantrolene-treated heart (n=6)

After 5 episodes of fibrillation-defibrillation in each heart, left ventricular tissue was analyzed for phosphorylation of RyR2 at Ser2014. Significant decrease in RyR2 phosphorylation normalized to GAPDH was observed in Dantrolene treated hearts, however, there was no difference in total RyR2 to GAPDH ratio between groups (FIG. 6).

After treatment with dantrolene sodium, systolic and diastolic blood pressure (sBP and dBP, respectively) significantly increased and remained higher than controls throughout the post-defibrillation period. Interestingly, sBP peaked at about 5 min post-defibrillation in Dantrolene group while the peak was not as pronounced in controls (approximately 98±17 mmHg vs. approximately 58±15 mmHg in controls, P<0.0003). Considering the more pronounced increase of BP Dantrolene-treated animals compared with controls, it can be proposed that Dantrolene significantly improved post-defibrillation contractile function and provided inotropic benefits through enhancing beta-adrenergic responsiveness of the myocardium (force-frequency relationship). Dantrolene improved force frequency relationship in failing human myocardium by enhancing cardiac contractility in the presence of sympathetic stimulation.[14] It was proposed that enhanced inotropic effect of isoproterenol in the presence of Dantrolene was due to modulation of diastolic i[$Ca^{2+}$] by Dantrolene.[14]

Interestingly, persistent elevation of diastolic i[$Ca^{2+}$] after prolonged VF has been reported in rabbit model of pacing-induced HF.[15,16] Though the exact mechanism has not been elucidated, this calcium cycling dysregulation and persistent elevation of i[$Ca^{2+}$] can be responsible for myocardial stunning post-VF. The benefit of beta-blockade during CPR has also been attributed in part to its effect on stabilization of RyR2.[17]

Recently, Dantrolene has been shown to bind to domain 601-620 of RyR2, a crucial modulator of cardiac contractility, in failed cardiomyocytes, stabilize the inter-domain interaction within the channel and significantly improve cardiac function.[12,13,18] Taken together, it can be concluded that Dantrolene protected cardiomyocytes, enhanced cardiac response to sympathetic stimulation post-defibrillation and provided inotropic benefits by modulating cardiac calcium cycling.

In addition, as demonstrated herein, defibrillation success and enhanced time to ROSC followed administration of dantrolene. In addition, dantrolene prevented the time-dependent disorganization of VF signals and enhanced defibrillation. Dantrolene-treated rabbit hearts were less susceptible to induction of VF with most successful VF episodes transformed to monomorphic VT or sinus rhythm in less than about 60 seconds.

Abnormal function of RyR2 in VF has been associated with CaA-ALT.[19] Despite the strong association between mechanical dysfunction of the heart and sudden death due to arrhythmias, the causal relationship is not well understood. Cardiac alternans has been linked to arrhythmogenesis and can be mediated by intracellular calcium handling. Given the integral role intracellular calcium plays in contractile function, calcium-mediated alternans may represent an important mechanistic link between mechanical dysfunction and electrical instability. This relationship, however, is not well understood due to complex feedback between membrane currents, intracellular calcium, and contraction. Through several pathways, calcium transient alternans is coupled to repolarization alternans that can form a substrate for reentrant excitation. Abnormal intracellular calcium cycling, either impaired release or impaired reuptake of sarcoplasmic reticulum calcium, is a cellular mechanism of calcium transient alternans. Thus, cardiac alternans is an important mechanistic link between mechanical dysfunction and sudden cardiac death.

Long duration of Calcium transients and disorganized Calcium cycling during VF has been proposed as a possible mechanism for LDVF.[20] It was shown that at 5 min of LDVF, Calcium transients became longer and more disorganized throughout epicardium and endocardium with significant CaA-ALT. It was concluded that alternans might have contributed to maintenance of VF. Lastly, it has been demonstrated that i[$Ca^{2+}$] and changes in Ca amplitude can indeed affect APD during VF and promote wave break.[21] Therefore, agents that modulate calcium cycling can enhance defibrillation success. In our study, rabbit hearts treated with Dantrolene were protected against CaA-ALT at fast heart rates compared to non-treated hearts. CaA-ALT was frequently observed in control hearts after 2 VF episodes. Interestingly, treatment with Dantrolene abolished the alternans developed after first VF in two hearts that were not initially treated with the drug and received Dantrolene later during second VF. Therefore, it can be proposed that Dantrolene played crucial role in restoring RyR2 function and decreased incidence of CaA-ALT.

Pigs treated with Dantrolene experienced fewer episodes and shorter duration of refibrillations. This effect can be due to restoration of myocardial calcium cycling by stabilization of RyR2. Hyperphosphorylation of RyR2 at Ser2808 and Ser2814 through PKA phosphorylation (sympathetic stimulation) and CaMKII phosphorylation (triggered by VF or fast heart rates) respectively is shown to result in diminished cardiac contractility and increased rate of sudden cardiac death and arrhythmias.[22-24] Theoretically the molecular changes (CaMKII and RyR2 hyperphosphorylation) that occur in the setting of pacing-induced HF can occur during VF as well. RyR2 was found to be hyperphosphorylated by CaMKII in a pig model of cardiac arrest.[7] Survival benefit of Esmolol administration during CPR has also been in part attributed to suppression of CaMKII-dependent RyR2 hyperphosphorylation in other studies.[7] Hyperphosphorylation of RyR2 leads to continuous diastolic calcium leak from the channel.[10,23,25] This leads to decreased SR calcium reserve and cause calcium overload.[26] Furthermore, continuous calcium leak and subsequent rise in cytosolic Calcium in diastole activates compensatory mechanisms (NCX activity) that cause after-depolarization, and eventually VF or refibrillations.[15,27,28] Thereby, RyR2 stabilizers such as Dantrolene can restore SR calcium reserve and provide antiarrhythmic benefits and prevent refibrillations.

We found a significant decrease in CaMKII-dependent RyR2 phosphorylation in Dantrolene-treated rabbit hearts. Furthermore, regulation of Calcium cycling by Dantrolene resulted in self-termination of VF in isolated rabbit hearts. The findings suggest that CaMKII phosphorylation of RyR2 is necessary for maintenance of VF and stabilizing the channel can lead to termination of VF. Kobayashi et al. established that Dantrolene binds with hyperphosphorylated RyR2 and stabilizes the channel by restoring the SR calcium reserve.[13] Therefore, the beneficial effects of Dantrolene in our in-vivo CPR model in terms of enhancing defibrillation and improving hemodynamic outcomes (cardiac contractility) can be explained by the direct impact of Dantrolene on stabilizing RyR2.

Exemplary Methods

In-Vivo Swine Model

Previously healthy 10-12 weeks-old Yorkshire pigs (n=24) were used. The protocol was approved by the Animal Care Committee of St. Michael's Hospital. Following endotracheal intubation anesthesia was maintained by continuous administration of Isoflurane (2% mixed with 100% O2) and ventilated (Ohio ventilator R.A.E. Technologies, Inc. Ontario) at 21 breaths/min and was continuously measured using CO2MO Plus monitoring system (Novametrix Medical Systems). Animals were continuously monitored using Lifepak 12 Medtronic-PhysioControl defibrillator for ECG monitoring. Two self-adhesive defibrillation pads were attached to the lateral aspects of the chest wall for defibrillation. (Medtronics Inc, Redmond, Wash.)

Electrophysiological and Hemodynamic Monitoring

Femoral arteries and veins were catheterized and an EP catheter (EP Technologies Inc, Sunnyvale, Calif.) was placed in the right ventricle to enable pacing and to induce VF. Two micro manometer-tipped Millar catheters (Millar Instruments, Inc, Houston, Tex.) were placed in Abdominal Aorta and right atrium. Pacing catheter was further attached to a custom designed signal acquisition and processing system. (Electrophysiological Recording system-Acqui2, Toronto, ON) The pressure and ECG signals were recorded at 1000 Hz with a 0.05 Hz high pass and 500 Hz low pass filter by custom software. (Acqui2, Cartesian Labs)

Experiment Protocol

After initial monitoring and stabilization, VF was induced by burst pacing (10V of 60 Hz current for 2 seconds) and left untreated for 4 minutes. Then, chest compression was started using a pneumatic device (Lucas, Jolife AB, Lund, Sweden) at 100 compressions/min and manual ventilation at 6 breath/min using 5-6 liters/min of 100% O2 with an AMBU bag was performed. CPR was continued for 3 minutes with no interruption of chest compressions. At the onset of CPR, animals received either a bolus dose of Dantrolene Sodium (2 mg/kg) or Isotonic Saline. At 7 min of VF, defibrillation was attempted at 150 J. If the animal failed to respond, defibrillation was attempted at 200 J (with stepwise increase to 300 J→360 J→360 J→360 J 360 J in case of failure) with 2 minute of CPR between shocks. After successful defibrillation, animals were monitored for 30 min to assess the outcome and occurrence of Refibrillations. At the end, survivors were sacrificed by inducing VF. If animals could not be defibrillated during refibrillation, the energy level was increased in a stepwise fashion to up to 4 attempts at 360 J.

In-Vivo Model Characterization

Refibrillation was defined as recurrence of VF after at least 5 beats of a non-VF rhythm following defibrillation. Survival was determined based on presence of sBP≥30 mmHg in abdominal aorta and normal sinus rhythm at the end of 30 min observation period. Time to Return of Spontaneous Circulation (ROSC) was calculated from the onset of CPR until sBP≥60 mmHg was attained in abdominal aorta after successful defibrillation. Sustained ROSC was defined as maintenance of sBP≥60 mmHg by the end of 30-min observation post-defibrillation. Ventricular ERP was measured at baseline and at 20 minutes into recovery (if any) via the S1-S2 stimulation method. Surface ECG signals at 4 min of VF and at 7 min of VF were extracted to analyze for VF organization. A Spatio-temporal index of VF organization (Regularity Index (RI)) was used. RI was defined as the ratio of the power at the Dominant Frequency (DF) to the total power. The power at the DF was calculated by summing the power values at the highest peak and its adjacent values (fixed band of 1 Hz). The total power was calculated as the sums over the range of 5-15 Hz. Values vary between 0 (disorganized) to 1 (highly organized).

Ex-Vivo Rabbit Model (Optical Mapping of APD, Calcium Transients and Protein Analysis)

New-Zealand white rabbits with weight ranging from 2.4-4.5 Kg were used. (n=14). All animals were anesthetized with sodium pentobarbital (35 mg/kg), aorta was attached to the Langendorff apparatus and retrogradely perfused with 37.5° C. oxygenated Tyrode solution with albumin 80 mg/L in deionized water equilibrated with 95% O2 and 5% CO2. Simultaneous optical mapping of epicardial surface of isolated hearts for Calcium and Voltage was performed using 0.5 mg Rhod2-AM and 10 microM/1 RH237. Blebbistatin at 10 microM/L was added to Tyrode solution to block cardiac contractions.

Experimental Protocol

VF was induced by burst pacing for 30 sec at 60 Hz and 10V and hearts were continuously perfused during VF. At 1 min of VF, a single dose of Dantrolene (10-20 μM/l) or isotonic saline was infused in the bubble trap. VF was monitored for 4 min and then defibrillated at 5 J. Five minutes after termination of first VF episode, 4 more episodes of fibrillation-defibrillation were tried on each heart with 5 min recovery time (in sinus rhythm) in between. VF duration for each VF episode was 4 min (or shorter in case of self-termination) followed by defibrillation. Inducibility (VF lasting for ≥10 sec) and Sustainability (VF lasting ≥60 sec) and total duration of these 4 VF episodes was measured and compared between Dantrolene and controls. Additionally, hearts were paced at various rates of 250, 220, 200, 180 and 160 msec Cycle Length (CL) for 30 seconds after first and second VF episodes. Simultaneous optical mapping of Calcium and voltage was performed during pacing to evaluate for Calcium Alternans. Calcium alternans was defined as beat-to-beat difference of more than 10% in Calcium wave amplitude. At the end of the experiment, LV tissue from the LV free wall was removed and frozen in liquid Nitrogen for further western blot analysis.

Western Blotting

Rabbit left ventricular homogenates were subjected to sodium dodecyl sulphate polyacrylamide gel electrophoresis (SDS-PAGE) on 4-15% Mini-PROTEAN gels. Proteins were transferred onto polyvinyl difluoride (PVDF) membranes, and blocked in 5% non-fat milk/Tris-buffered saline Tween20 (TBST). For immunoreaction, blots were probed with anti-RyR2 (1:4,000; Pierce) and anti-pS2814-RyR2 (1:3,000; Badrilla) antibodies. Immunodetection was carried out with horseradish peroxidase (HRP) conjugated secondary antibodies: anti-mouse (Cell Signalling) and anti-rabbit (Santa Cruz), respectively. Bands were exposed to X-ray films, visualized with Western Lightning (PerkinElmer), and quantified using densitometry and Quantity One Software (Bio-Rad). Protein expressions were normalized to levels of GAPDH (1:8,000; Santa Cruz).

Statistical Analysis

Mean time to ROSC, mean time to successful defibrillation, onset of refibrillation and regularity index of VF at different time points were analyzed using unpaired student t-test. Repeated-measures ANOVA was used to compare continuous variables between groups at different time points. Protein phosphorylation analysis and comparison of ordinal variables (number of refibrillations) were performed using Wilcoxon Mann-Whitney test. Repeated measures logistic regression was used to compare the incidence of consecutive induced and sustained VF episodes in the rabbit hearts. P<0.05 was considered statistically significant. All statistical analysis were performed using Stata 11.1 (Stata Corp LP)

IV. INCORPORATION BY REFERENCE

The contents of all references, patents, pending patent applications and published patents, cited throughout this application are hereby expressly incorporated by reference.

V. EQUIVALENTS

Those skilled in the art will recognize, or be able to ascertain using no more than routine experimentation, many equivalents to the specific embodiments of the invention described herein. Such equivalents are intended to be encompassed by the following claims.

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

What is claimed is:

1. A method for treatment of cardiac dysfunction comprising administering to a subject in need thereof a therapeutically effective amount of at least one of dantrolene, azumolene, a dantrolene analog, pharmaceutically acceptable salt thereof or a combination thereof approximately during or following cardiac arrest, wherein the method is effective in treating or protecting from at least one cardiac arrest-related dysfunction including cardiac arrhythmia, premature ventricular contraction (PVC) induced left ventricular dysfunction, atrial fibrillation induced left ventricular dysfunction, ventricular arrhythmia, and a combination thereof.

2. The method of claim 1, wherein the ventricular arrhythmia is a ventricular tachycardia (VT) or ventricular fibrillation (VF).

3. The method of claim 1, wherein the step of administering a therapeutically effective amount of dantrolene, azumolene, a dantrolene analog, pharmaceutically acceptable salt thereof or combination thereof, is performed contemporaneously with or following a step of performing cardiopulmonary resuscitation (CPR), defibrillation or both.

4. The method of claim 1, wherein the effective amount of dantrolene or azumolene is from 0.1 µg/kg/day to about 1000 mg/kg/day.

5. The method of claim 1, wherein a therapeutic effective amount of at least one additional anti-arrhythmic agent is co-administered prior, contemporaneously, or subsequent to administration of the therapeutically effective amount of dantrolene, azumolene, a dantrolene analog, pharmaceutically acceptable salt thereof or combination thereof.

6. The method of claim 1, wherein the method further effectuates at least one of an improvement in the time-dependent temporal disorganization of VF, enhanced defibrillation success, an improvement in hemodynamic performance, improved sinus rhythm after defibrillation, improvement in sustained return of spontaneous circulation (ROSC), reduction of time to ROSC, improved post-defibrillation systolic blood pressure, improved post-defibrillation diastolic blood pressure, reduced time to successful defibrillation, reduced energy needed for defibrillation, reduced number of defibrillations required, reduced duration of fibrillation, improved survival rate, improved cardiac contractility, reduction in refibrillations, reduction in calcium amplitude alternans (CaA-ALT), reduction in RyR2 hyperphosphorylation, reduction in RyR2 calcium leak, increased resistance to VF induction, improved survival or a combination thereof.

7. A method for acute treatment of cardiac arrest comprising:
   (i) performing CPR or defibrillation or both on a subject in need thereof;
   (ii) administering a therapeutically effective amount of at least one of dantrolene sodium, azumolene or a combination thereof to the subject approximately contemporaneously with or subsequent to performing step (i), wherein the method is effective for abrogating or ameliorating a detrimental effect of cardiac arrest.

8. The method of claim 7, wherein the detrimental effect of cardiac arrest is ventricular arrhythmia.

9. The method of claim 8, wherein the ventricular arrhythmia is a ventricular tachycardia (VT) or ventricular fibrillation (VF).

10. The method of claim 7, wherein the method further effectuates at least one of a reduction in RyR2 hyperphosphorylation, a reduction in calcium alternans, a reduction in refibrillations, an improvement in cardiac contractility, an improvement in ROSC, an improvement in hemodynamic function, a reduction in morbidity, a reduction in mortality, or a combination thereof.

11. A method for the treatment of premature ventricular contraction (PVC) induced left ventricle (LV) dysfunction in a subject in need thereof comprising administering a therapeutically effective amount of at least one of dantrolene sodium, azumolene or a combination thereof to the subject approximately during or following a PVC event, wherein the method is effective in treating or preventing PVC induced LV dysfunction.

12. The method of claim 11, wherein the effective amount of dantrolene sodium or azumolene is from 0.1 µg/kg/day to about 1000 mg/kg/day.

13. The method of claim 11, wherein the method comprises co-administering an effective amount of at least one additional anti-arrhythmic agent prior, contemporaneously, or subsequent to administration of the therapeutically effective amount of dantrolene sodium, azumolene or combination thereof, wherein the combination is effective in treating or preventing PVC.

14. A method for the treatment of atrial fibrillation (AF) induced left ventricle (LV) dysfunction in a subject in need thereof comprising administering a therapeutically effective amount of at least one of dantrolene sodium, azumolene or a combination thereof to the subject approximately during or following AF, wherein the method is effective in treating or preventing AF induced LV dysfunction.

15. The method of claim 14, wherein the effective amount of dantrolene sodium or azumolene is from 0.1 µg/kg/day to about 1000 mg/kg/day.

16. The method of claim 15, wherein the method comprises co-administering an effective amount of at least one additional anti-arrhythmic agent prior, contemporaneously, or subsequent to administration of the therapeutically effective amount of dantrolene sodium, azumolene or combination thereof, wherein the combination is effective in treating or preventing AF induced LV dysfunction.

\* \* \* \* \*